United States Patent [19]

Acharya et al.

[11] Patent Number: 6,075,835
[45] Date of Patent: Jun. 13, 2000

[54] METHODS AND APPARATUS FOR IMAGING SYSTEM QUALITY READINESS CHECK

[75] Inventors: Kishore Acharya; Diane M. Miesbauer, both of Brookfield; Shibu P. Pillai, Waukesha; Charles Shaughnessy, Whitefish Bay, all of Wis.

[73] Assignee: General Electric Company, Milwaukee, Wis.

[21] Appl. No.: 09/140,301

[22] Filed: Aug. 25, 1998

[51] Int. Cl.$^7$ ........................................................ A61B 6/03
[52] U.S. Cl. .................................. 378/4; 378/19; 378/901
[58] Field of Search ................................. 378/4, 15, 19, 378/901

[56] References Cited

U.S. PATENT DOCUMENTS 4,472,823   9/1984   Waltham .................................. 378/19

*Primary Examiner*—David V. Bruce
*Attorney, Agent, or Firm*—Armstrong, Teasdale; Christian G. Cabou; Phyllis Y. Price

[57] ABSTRACT

The present invention, in one form, is an imaging system which, in one embodiment, utilizes scan data and DAS input signals to determine image quality. More specifically, and in one embodiment, by generating a ratio of data from two scans, a group of non-conforming detector cells may be identified. In addition, by comparing scans performed at different time frames, a trend of image quality is also determined. In addition, a group of non-conforming DAS channels may be identified by applying a range of known input signals. By comparing the an absolute gain ratio, the DAS performance is determined.

26 Claims, 7 Drawing Sheets

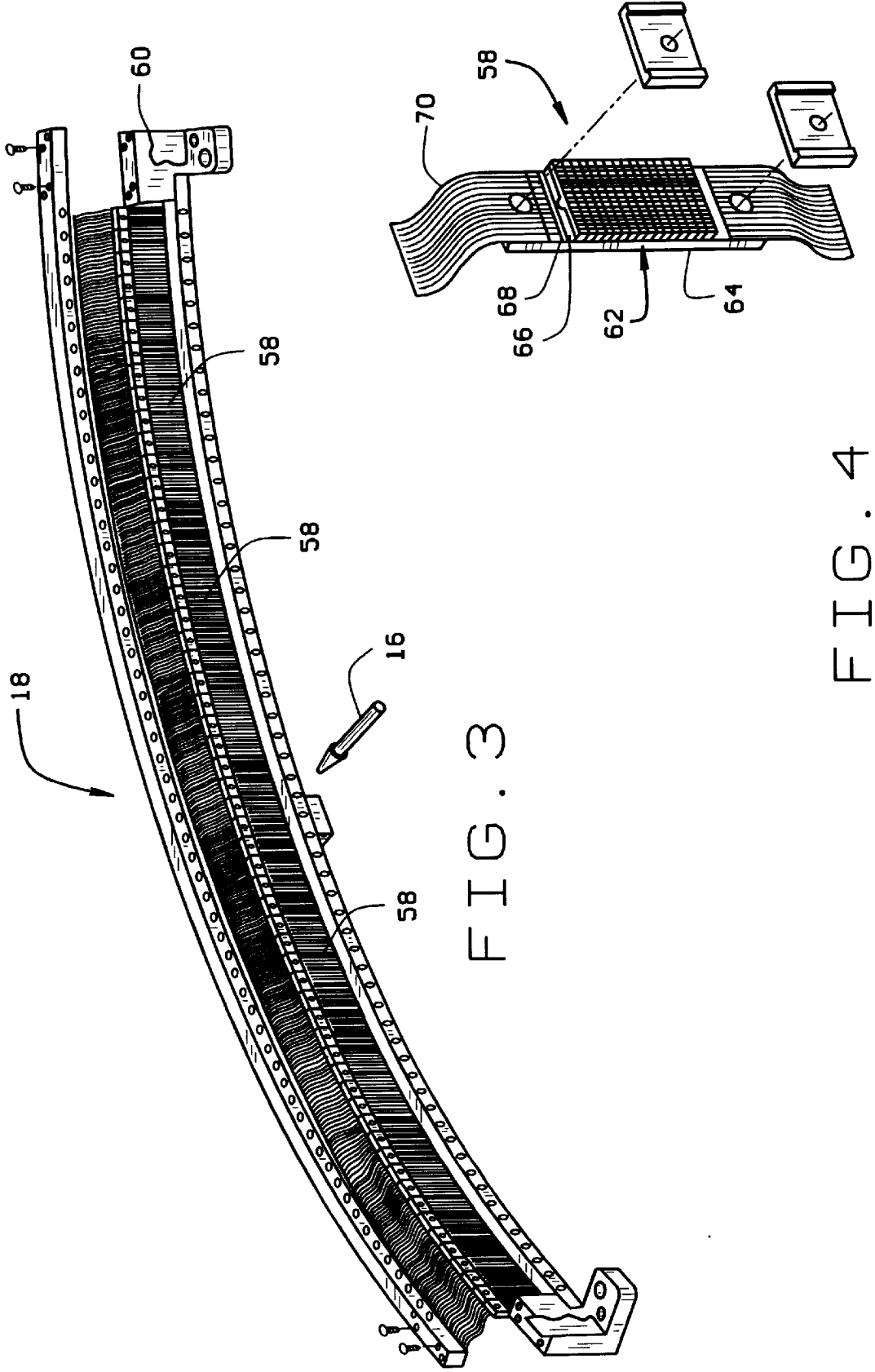

METHODS AND APPARATUS FOR IMAGING SYSTEM QUALITY READINESS CHECK

BACKGROUND OF THE INVENTION

This invention relates generally to computed tomography (CT) imaging and more particularly, to image quality verification of an imaging system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

At least one known CT imaging system utilizes a detector array and a data acquisition system (DAS) for collecting image data. The detector array includes detector cells or channels that each produce an analog intensity signal which is representative of the x-ray energy impinged upon the cell. The analog signals are then supplied to the DAS for conversion to digital signals. The digital signals are then used to produce image data. Image artifacts, with the potential for patient mis-diagnosis, can be produced by the degradation or failure of individual detector cells and the DAS. Detector cell degradation as measured by gain non-linearity typically produces ring or band annoyance artifacts. In addition, failure of cells at the center of the detector results in a spot on the image, which could be interpreted as a tumor or lesion. Similarly, degradation and failure of the DAS impacts the image quality.

Accordingly, it is desirable to provide an imaging system which detects degradation and failure of the detector array and the DAS. It would also be desirable to provide such a system without increasing the cost and complexity of the system.

BRIEF SUMMARY OF THE INVENTION

These and other objects may be attained in an imaging system which, in one embodiment, utilizes scan data and DAS input signals to determine image quality. The imaging system includes a detector array having a plurality of detector cells, an x-ray source for radiating an x-ray beam toward the detector array, and a data acquisition system (DAS). A detector cell intensity signal is generated as the x-ray beam impinges the detector cell. A scan is generated by utilizing the DAS to convert a plurality of detector cell intensity signals into data. The scan data is utilized to determine image quality.

More specifically, by generating a ratio of data from two scans, a group of non-conforming detector cells may be identified. Particularly, a present scan data to reference scan data ratio is generated. In addition, by comparing scans performed at different time frames, i.e., days or weeks apart, a trend of image quality of the imaging system is also determined. In addition, a group of non-conforming DAS channels may be identified by applying a range of known reference input signals to the DAS. By evaluating an absolute gain ratio, the DAS performance is determined.

By utilizing the scan data and reference DAS input signals, image quality is determined. In addition, an image quality trend is generated. Further, the described system produces repeatable results without requiring the scanning of phantoms or operator intervention so that the cost and complexity of the system are not increased.

BRIEF DESCRIPTION OF THE DRAWINGS

FIG. 3 is a perspective view of a CT system detector array.

FIG. 4 is a perspective view of a detector module.

DETAILED DESCRIPTION OF THE INVENTION

Figure 1:
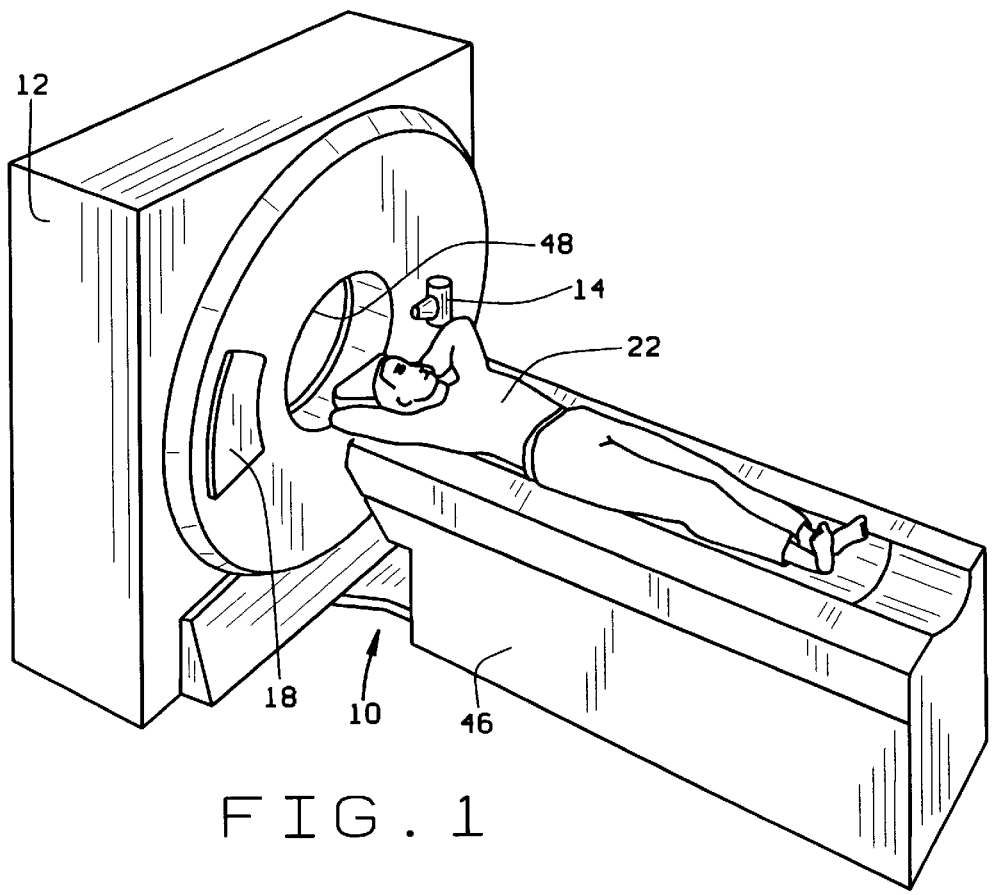
FIG. 1 is a pictorial view of a CT imaging system.
Figure 2:
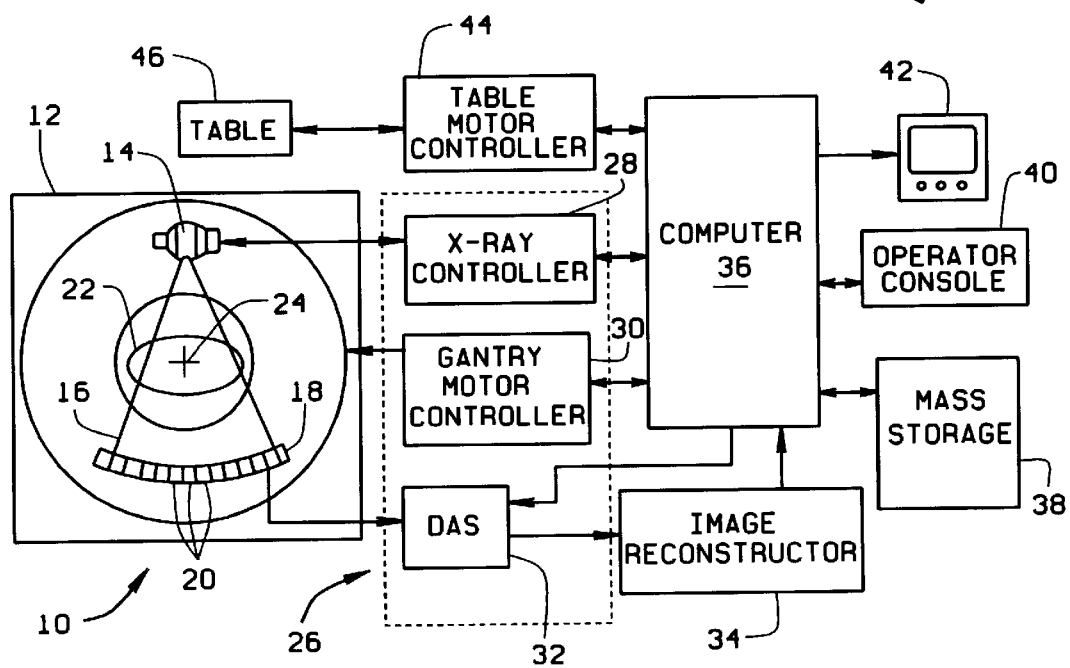
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements, or cells 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A scaleable data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives and supplies signals via a user interface, or graphical user interface (GUI). Specifically, computer receives commands and scanning parameters from an operator via console 40 that has a keyboard and a mouse (not shown). An associated cathode ray tube display 42 allows the operator to observe the reconstructed image and other data from computer 36. The operator supplied commands and parameters are used by computer 36 to provide control signals and information to x-ray controller 28, gantry motor controller 30, DAS 32, and table motor controller 44.

As shown in FIGS. 3 and 4, detector array 18 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of the photodiode array are electrically connected to DAS 32, resulting in 16 separate, simultaneous slices of data being sent to DAS 32. Of course, many other slice combinations are possible.

In one specific embodiment, detector 18 includes fifty-seven detector modules 58. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5A:
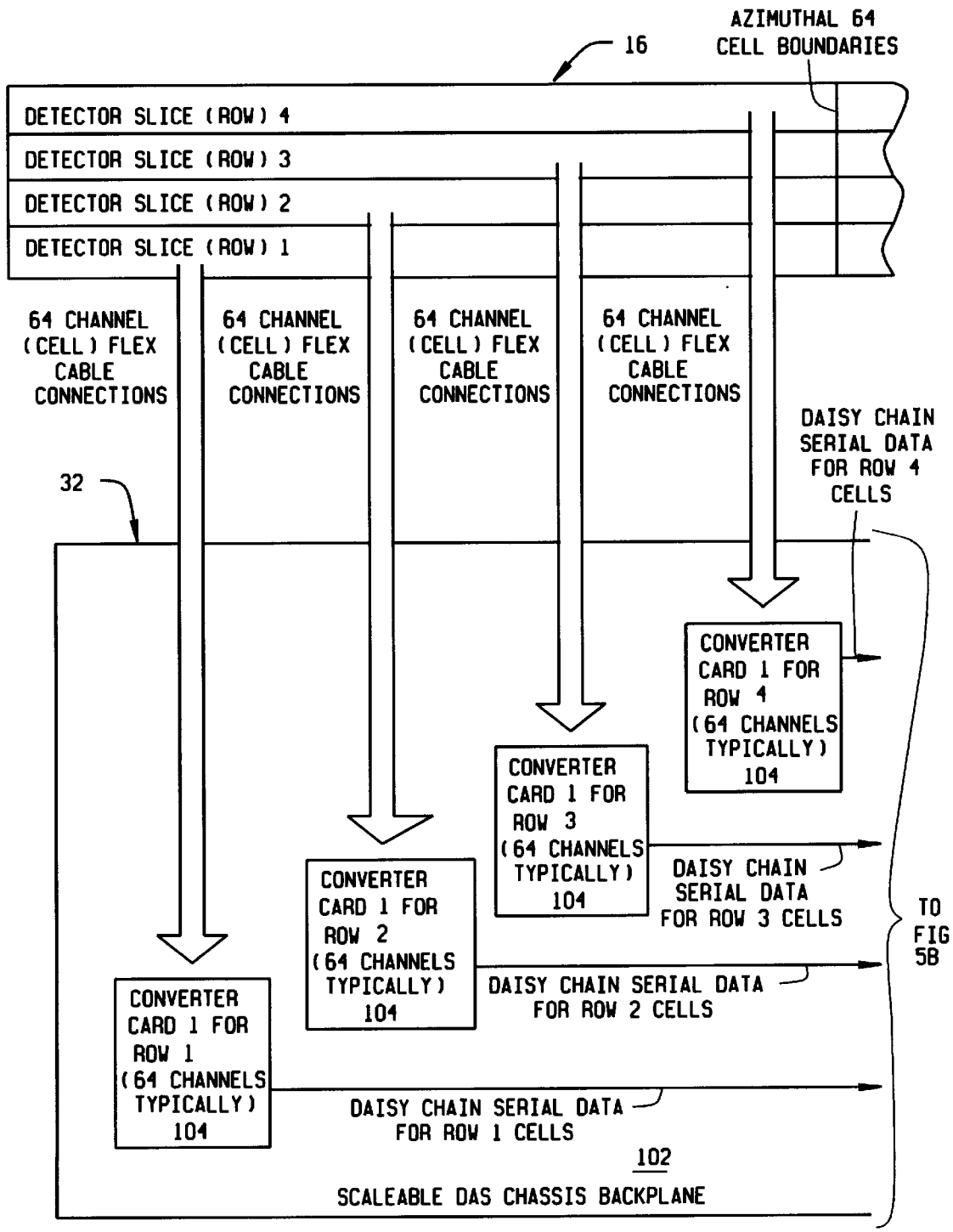
FIGS. 5A, 5B, and 5C together form a block diagram of a scaleable data acquisition system of the CT imaging system shown in FIG. 1.
Figure 5B:
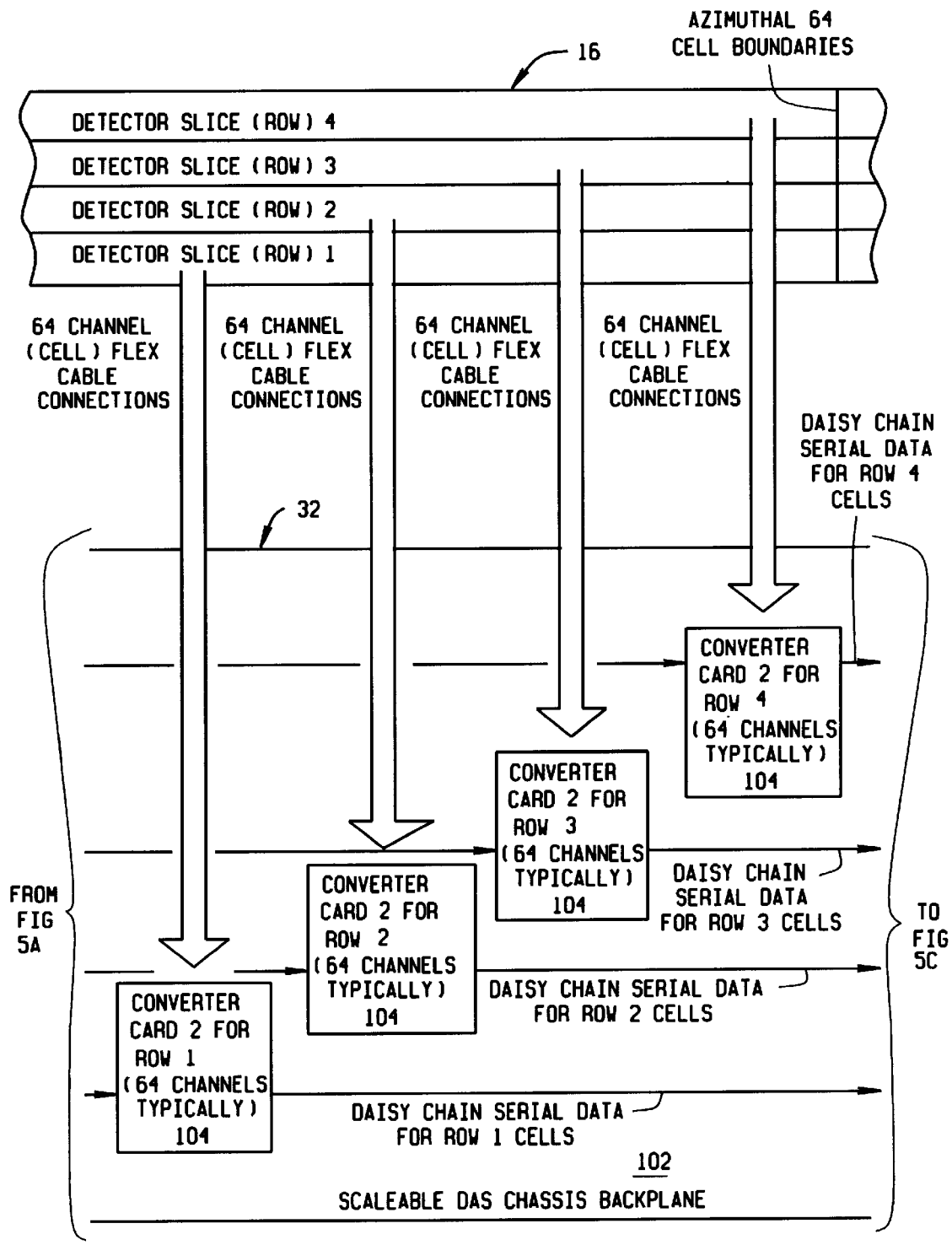
Figure 5C:
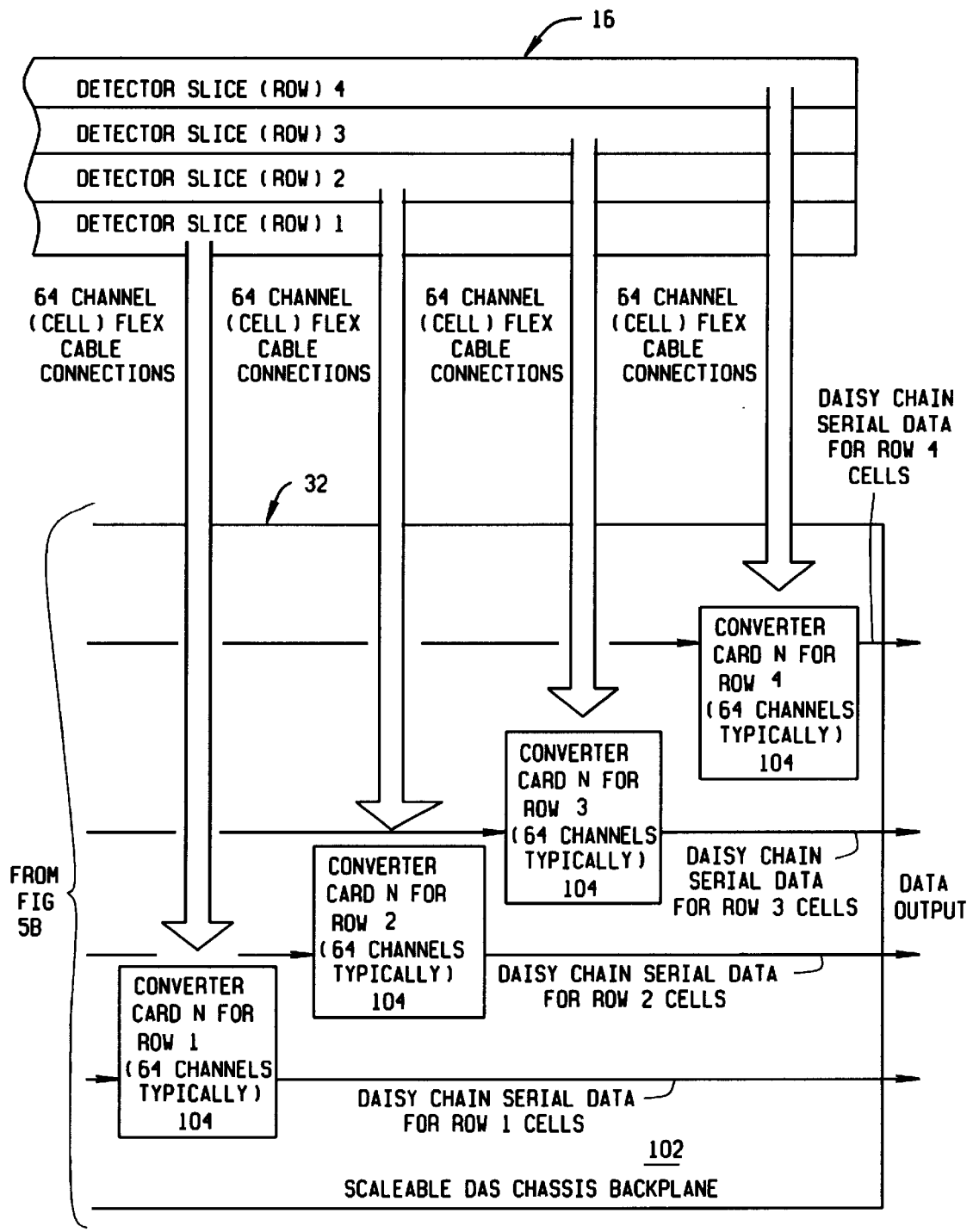

FIGS. 5A, 5B, and 5C together form a block diagram of scalable data acquisition system (SDAS or DAS) 32 which is easily reconfigured to be used with either single slice or multi-slice CT detector systems. SDAS 32 can be reconfigured by adding or removing printed circuit boards to accommodate the number of slices provided by x-ray detector 18. SDAS 32 is configured to convert the low level electrical current signal, or intensity signals, from x-ray detector 18 to digital values for image reconstruction, display and archive. Single slice third generation, fan-beam CT systems have traditionally contained 300 to 1000 detector cells in the Azimuthal direction. SDAS 32 correspondingly is required to provide an anti-alias filter (not shown) for each cell prior to Analog to Digital Conversion (ADC). DAS cells are traditionally referred to as channels. Detector cells can be ganged or paralleled to one DAS channel. The digital output from DAS 32 is usually transmitted either in a serial or semi-serial fashion, as described below in more detail, to reduce the amount of interconnecting hardware. Analog current signals from detector 18 are supplied to input channels (not shown) of SDAS 32 via shielded ribbon or flex cables (not shown). The cables are connected to SDAS 32 at a DAS backplane 102. DAS Converter boards 104 are also plugged into DAS backplane 102. This interconnection provides several advantages. First, backplane 102 enables ganging the detector cells on the outside edges of the fan beam. Second, backplane 102 allows a redistribution of the detector cells to appropriate converter boards 104. Signals from more than one slice are contained in the same flex cable. Each converter board 104 only serves one slice since the reconfiguration of DAS 32 from one multi-slice configuration to another or to the single slice configuration requires only the removal or addition of converter boards 104. Third, backplane 102 enables a blending or weaving of DAS channels and detector cells near the end channels of a converter board 104.

Another aspect of the SDAS 32 is converter boards 104 which combine the anti-alias filter and ADC on the same board rather on separate boards. Having the filter and ADC on the same board 104 enables the modularity required for scalable DAS 42. The integrated filter-ADC function on the same board also limits the possibility of electromagnetic and conducted interference because of short electrical lead lengths.

Figure 6A:
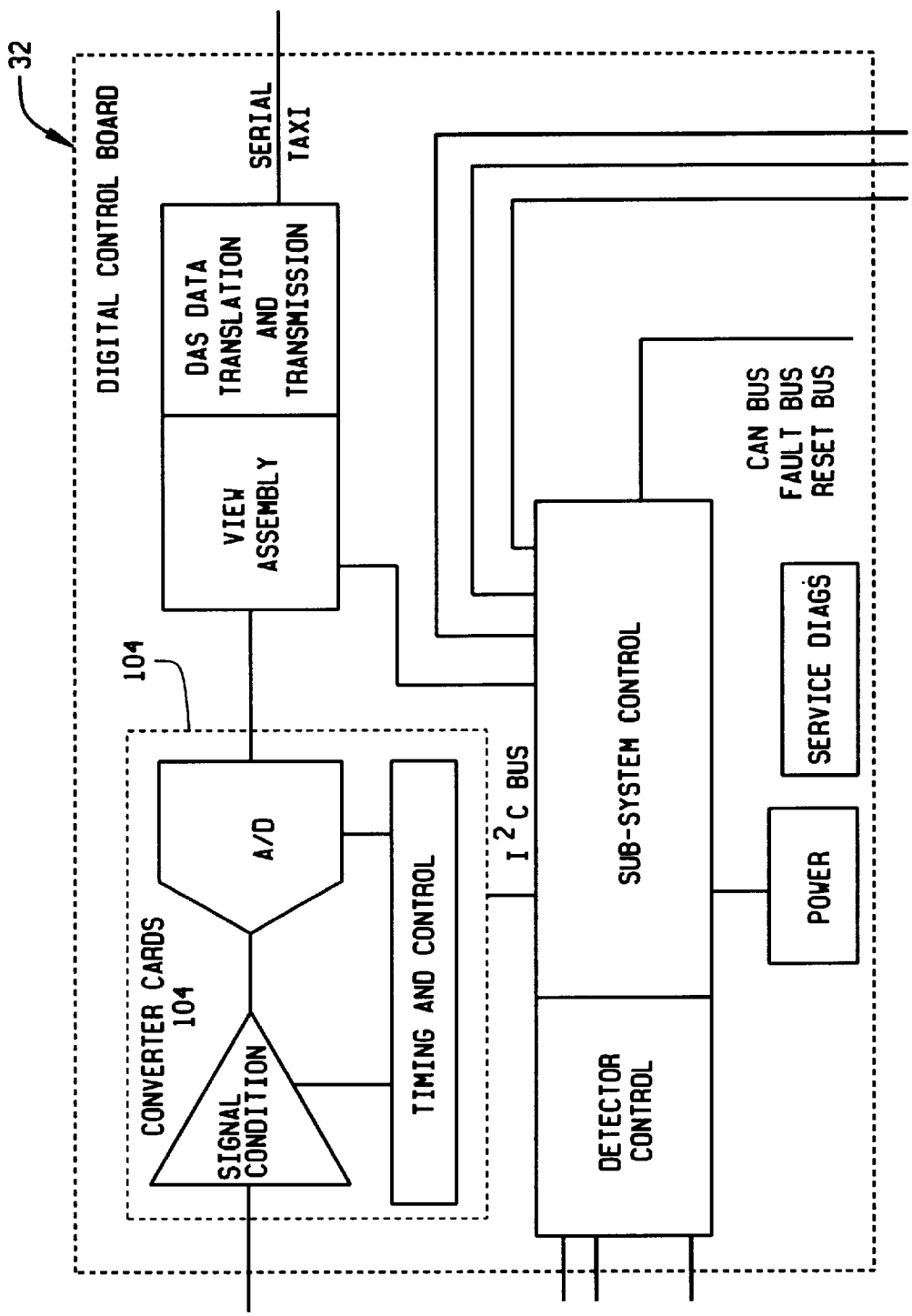
FIGS. 6A and 6B together form a functional block diagram of the scaleable data acquisition system shown in FIGS. 5A, 5B, and 5C.
Figure 6B:
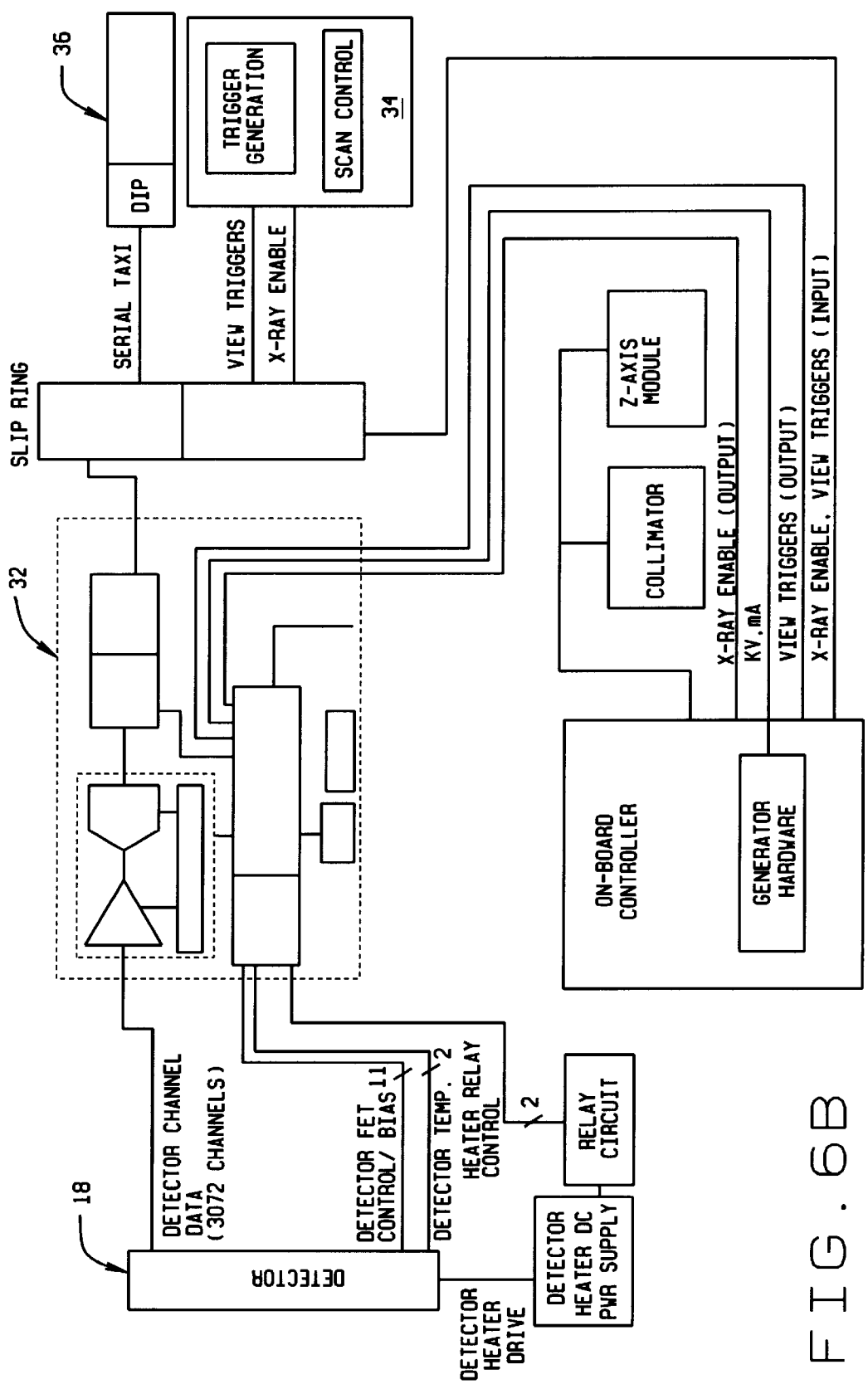

FIGS. 6A and 6B together form a functional block diagram of SDAS 32. As explained above, SDAS 32 processes low level analog signals from detector 18 into digital data.

Once in digital form, the signal is manipulated and transmitted to computer 36 for storage. Several signal adjustments can be made via control registers contained on each converter board 104. For diagnostic purposes, SDAS 32 is configured to enable and set a special analog test voltage into the signal conditioning stage of the converter boards. In one embodiment, the test voltage will be programmable in 16384 steps between 0 and −3 volts. It is used in the diagnosis of the S-DAS acquisition and signal processing chain. The analog test signal can be enabled to either the input of the pre-amplifiers, or to a special test input channel. The firmware is further configured to set a I to 16 multiplication factor with respect to the test voltage when it is enabled into the pre-amplifier stage. The Analog to Digital (A/D) Converter block converts each supplied analog voltage to a digital word linearly proportional to the input signal level. In one embodiment, the outputs are read once per view and sent to computer 36. Additional details regarding the above described multislice imaging system are set forth in co-pending U.S. patent application Ser. No. (15-CT-4641), entitled Scalable Multislice Imaging System, which is assigned the present assignee and hereby incorporated herein, in its entirety, by reference.

In one embodiment, the image quality of system 10 is verified, or determined by performing an image quality readiness check algorithm. The image quality readiness check algorithm determines conformance of collected scan data with respect to known good reference scan data. By comparing the data from different scans, a deviation determination may be made so that a non-conformance prediction may be determined. The readiness check algorithm includes verifying the passage of x-ray beam 16 through detector array 18 and DAS 32 generates data values within selected limits (identified as SMART TREND), and verification of DAS 32 without any contribution from detector array 18 (identified as DC CAL).

SMART TREND

The performance of detector array 18 and DAS 32 are verified by comparing scan data from at least two different periods of time so that an image quality check is determined. In one embodiment, the scan data representing the actual performance today is compared to the scan data representing the performance of a reference period of time, for example, a baseline or prior period, i.e., yesterday or last month. The scan data is generated by performing a scan, for example an air scan, so that x-ray beam 16 is radiated toward detector array 18. As described above, the impingement of beam 16 on detector array 18 generates intensity signals which are supplied to DAS 32 for conversion into image data. More specifically and in one embodiment, a baseline scan is performed when system 10 is first commissioned, immediately following replacement or calibration of components, for example, x-ray source 14, detector array 18, and DAS 32, or at a selected time interval, i.e., every 30 days. Following generation of the scan data, the data is view averaged, offset corrected, and reference channel normalized, as known in the art, to generate baseline scan data. In one embodiment, a time stamp or time reference is included in the baseline scan data so that the time of the scan is determinable.

During operation of system 10, an actual performance scan may be performed to generate an actual data set. The actual scan data set is generated in a similar manner to the baseline data set, i.e., view averaged, offset corrected, and channel normalization. The image quality of detector array 18 and DAS 32 are then verified or determined by comparing the reference, or baseline, data set and the actual data set. By comparing the two data sets, cells of detector array 18 and channels of DAS 32 may be identified to be outside of defined, or selected values or tolerances. In one embodiment, the generated reference data set and the generated actual data set are used to identifying a group of non-conforming detector cells. Specifically, the identified non-conforming detector cells of detector 18 may include any number of cells which do not meet the defined performance characteristics. For example, if, by comparing the reference data set and the actual data set, all cells of detector array 18 are within the defined or selected performance characteristic values, the identified group would contain zero cells, indicating all cells are functioning properly. If, however, one or more of the cells fail to meet the defined characteristic values, the cells would be identified in the group of nonconforming cells. Utilizing the identified group information, specific action may be taken, for example replacement of detector array 18 or replacement of specific detector modules 58.

In addition to comparing image quality of system 10 to the baseline scan data set, the image quality of system 10 may be compared to a prior data set, for example, the data set from yesterday. The data set from yesterday may be determined by examining the time stamp of a stored data set, for example, stored in a memory of computer 36. By comparing the data set from the current day to the data set from previous day (yesterday) and the baseline data set, a short-term performance characterization, or short-term trend, and a long term performance characterization, or long-term trend, may be determined. The trends may be utilized to determine, for example, replacement actions to avoid failures.

Specifically and in one embodiment, to identify the group of detector cells, a ratio of the actual data set and the reference data set is generated. More specifically, a first ratio data set is generated and includes a ratio value for each data element of the actual data set and the baseline data set, for example the ratio of a data element representative of the intensity signals for defined detector cell for the two different periods of time. Similarly, a second ratio data set is generated and includes a ratio value for each data element of the actual data set and the first time data set, or the data set from yesterday.

The first ratio data set and the second ratio data set are then processed by applying a filter to the respective data sets. More specifically, the first ratio data set and the second ratio data set are each filtered using a high pass filter and a low pass filter. Particularly, the high pass filter is applied to the first ratio data set to generate a first filtered ratio data set and the low pass filter is applied to the first ratio data set to generate a second filtered ratio data set. Then, the high pass filter is applied to the second ratio data set to generate a third filtered ratio data set and the low pass filter is applied to the second ratio data set to generate a fourth filtered ratio data set. In addition, a first difference data set is determined, or generated, for adjacent channels of the first ratio data set and a second difference data set is determined, or generated for adjacent channels of the second ratio data set.

The first ratio data set and the second ratio data set are then evaluated, or verified, to identify the group of non-conforming cells of detector array 18. More specifically, a determination is made if the first ratio data set equals a first selected value, for example, about approximately 1 (1 plus a noise factor plus a drift factor plus a gross error factor). Similarly, a determination is made whether the second ratio data set equals a selected value, for example a value similar to the first selected value). Particularly, each data value, or channel, of the first filtered ratio data set, second filtered ratio data set, third filtered ratio data set, fourth filtered ratio data set, first difference data set, and second difference data set (data sets may also be referred to vectors) is evaluated, or limit checked. Each channel may have an unique value or specific regions of detector 18 may have common limit values. For example, center channels of cells of detector array 18 may have tighter tolerances than the tolerance of the cells located near the ends of array 18. By utilizing the value limits, an operator or service technician may evaluate the image quality of system 10. In addition to determining operational capability, short term and long term performance may be evaluated by comparing the present day scan to the prior day and the baseline scans. As a result, each cell of detector array 18 is verified without scanning an object.

In another embodiment, a bow-tie scan may be performed in a manner similar to the above described air scan. Specifically, x-ray beam 16 is filtered using a bow-tie filter (not shown) so that the shape of x-ray beam 16 is altered. Short term performance is then determined as described above for the filtered x-ray beam.

DC CAL

In addition to the identification of the group of detector cells, the present invention identifies a group of DAS channels based on DAS input signals. More specifically, known DAS input signals are injected to, or supplied to the DAS channels to generate DAS digital output signals while the gantry is stationary. The DAS output signals are then determined to be within selected, or pre-defined values to identify non-conforming DAS channels. More specifically, a first DAS input signal is injected into a selected DAS channel so that a first DAS data value is determined, or generated. The generated first DAS data value is then evaluated, or compared to a selected value. In one embodiment, a series of DAS input signals are applied to each DAS channel to determine image quality, i.e., output signal levels, for different input voltages. For example, seven different input signals are applied to each DAS channel. The seven levels are determined so that a first input signal is a minimum value and the seventh value is a maximum value. The seven value is converted by DAS 32 so that an absolute data value is generated. The absolute gain value for each channel is then compared to determine if the value is within a selected or defined limit value. Absolute gain, or DAS ratio data is then determined for each channel based on the six non-maximum voltages (DAS data set) and the absolute ratio data value.

The DAS ratio is then compared to determine if the DAS ratio is within a DAS selected, or pre-defined, value. In addition, first differential data is generated for adjacent channels of DAS ratio data. The first differential data is then compared to determine if the data is equal to a first differential selected value, or tolerance.

By utilizing the described DC CAL and SMART TREND algorithm, the image quality of detector array 18 and DAS 32 is determined. More specifically, in addition to determining operational image quality, the described procedure determines performance trends of detector array 18. In one embodiment, the described procedure is executed in the background during daily system preparation along with tube warm up and calibration, and may be executed without scanning phantoms or require operator intervention.

The above described system verifies image quality utilizing scan data and reference DAS input signals. In addition, to verifying image quality, the present invention generates a image quality trend. Further, the described system produces repeatable results without requiring the scanning of phantoms or requiring operator intervention.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, the systems described may be used with any single or multislice system. In addition, the image quality procedure described above may be implemented in an algorithm stored in computer 36 or in a separate host computer. Accordingly, the spirit and scope of the invention are to be limited only by the terms of the appended claims.

What is claimed is:

1. A method of determining image quality in an imaging system, the imaging system including an x-ray source for emitting an x-ray beam and scanning an object of interest, the system using projection data to reconstruct an image of the object, the system further including a detector having at least two detector cells configured to generate actual intensity signals when impinged by the x-ray beam, said method comprising the steps of:

generating at least one reference data set;

generating an actual data set; and identifying a group of detector cells based on the generated reference data set and the generated actual data set.

2. A method in accordance with claim 1 wherein generating the reference data set comprises the steps of:

generating a baseline data set; and generating a first time data set.

3. A method in accordance with claim 2 wherein identifying a group of detector cells based on the generated reference data set and the generated actual data set comprises the steps of:

generating first ratio data based on the actual data set and the baseline data set; and generating second ratio data based on the actual data set and the first time data set.

4. A method in accordance with claim 3 further comprising the steps of filtering the first ratio data and filtering the second ratio data.

5. A method in accordance with claim 4 wherein filtering the first ratio data and filtering the second ratio data comprises the steps of:

applying a high pass filter to the first ratio data to generate first filtered ratio data;

applying a low pass filter to the first ratio data to generate second filtered ratio data;

applying a high pass filter to the second ratio data to generate third filtered ratio data; and applying a low pass filter to the second ratio data to generate fourth filtered ratio data.

6. A method in accordance with claim 3 further comprising the steps of:

determining first difference data for adjacent channels of first ratio data; and determining second difference data for adjacent channels of second ratio data.

7. A method in accordance with claim 3 wherein identifying a group of detector cells based on the generated reference data set and the generated actual data set further comprising the steps of:

determining if the first ratio data equals a first selected value; and determining if the second ratio data equals a second selected value.

8. A method in accordance with claim 7 wherein the first selected value is about approximately one.

9. A method in accordance with claim 7 wherein the second selected value is about approximately one.

10. A method in accordance with claim 1 wherein the imaging system further includes a data acquisition system having a plurality of channels configured to generate a DAS data set from DAS input signals, and wherein said method further comprising the step of identifying a group of data acquisition system channels based on the DAS input signals.

11. A method in accordance with claim 10 wherein identifying the group of data acquisition system channels based on the DAS input signals comprises the steps of:

determining a first DAS data value for a first DAS input signal; and determining a DAS data set for at least a second DAS input signal; and generating DAS ratio data based on the first DAS data value and the DAS data set.

12. A method in accordance with claim 11 further comprising the step of determining whether the DAS ratio data equals a first DAS selected value.

13. A method in accordance with claim 11 further comprising the steps of:

generating first differential data for adjacent channels of DAS ratio data; and determining whether the first differential data equals a first differential selected value.

14. A system of determining image quality in an imaging system, the imaging system including an x-ray source for emitting an x-ray beam and scanning an object of interest, the system using projection data to reconstruct an image of the object, the system further including a detector having at least two detector cells configured to generate actual intensity signals when impinged by the x-ray beam, said system configured to:

generate at least one reference data set;

generate an actual data set; and identify a group of detector cells based on the generated reference data set and the generated actual data set.

15. A system in accordance with claim 14 wherein to generate the reference data set, said system configured to:

generate a baseline data set; and generate a first time data set.

16. A system in accordance with claim 15 wherein to identify a group of detector cells based on the generated reference data set and the generated actual data set, said system configured to:

generate first ratio data based on the actual data set and the baseline data set; and generate second ratio data based on the actual data set and the first time data set.

17. A system in accordance with claim 16 further configured to filter the first ratio data and filter the second ratio data.

18. A system in accordance with claim 17 wherein to filter the first ratio data and filter the second ratio data, said system configured to:

apply a high pass filter to the first ratio data to generate first filtered ratio data;

apply a low pass filter to the first ratio data to generate second filtered ratio data;

apply a high pass filter to the second ratio data to generate third filtered ratio data; and apply a low pass filter to the second ratio data to generate fourth filtered ratio data.

19. A system in accordance with claim 16 further configured to:

determine first difference data for adjacent channels of first ratio data; and determine second difference data for adjacent channels of second ratio data.

20. A system in accordance with claim 16 wherein to identify a group of detector cells based on the generated reference data set and the generated actual data set, said system further configured to:

determine if the first ratio data equals a first selected value; and determine if the second ratio data equals a second selected value.

21. A system in accordance with claim 20 wherein the first selected value is about approximately one.

22. A system in accordance with claim 20 wherein the second selected value is about approximately one.

23. A system in accordance with claim 14 wherein the imaging system further includes a data acquisition system having a plurality of channels configured to generate a DAS data set from DAS input signals, and wherein said system further configured to identify a group of data acquisition system channels based on the DAS input signals.

24. A system in accordance with claim 23 wherein to identify the group of data acquisition system channels based on the DAS input signals, said system configured to:

determine a first DAS data value for a first DAS input signal; and determine a DAS data set for at least a second DAS input signal; and generate DAS ratio data based on the first DAS data value and the DAS data set.

25. A system in accordance with claim 24 further configured to determine whether the DAS ratio data equals a first DAS selected value.

26. A system in accordance with claim 24 further configured to:

generate first differential data for adjacent channels of DAS ratio data; and determine whether the first differential data equals a first differential selected value.

* * * * *